United States Patent
Avivi et al.

(10) Patent No.: US 11,628,187 B2
(45) Date of Patent: Apr. 18, 2023

(54) ***SPALAX* FIBROBLAST-DERIVED ANTI-CANCER AGENTS**

(71) Applicant: CARMEL-HAIFA UNIVERSITY ECONOMIC DEVELOPMENT CORP. LTD., Haifa (IL)

(72) Inventors: Aaron Avivi, Misgav (IL); Imad Shams, Majdal Sham (IL); Irena Manov, Haifa (IL)

(73) Assignee: CARMEL-HAIFA UNIVERSITY ECONOMIC CORP. LTD., Haifa (IL)

( * ) Notice: Subject to any disclaimer, the term of this patent is extended or adjusted under 35 U.S.C. 154(b) by 777 days.

(21) Appl. No.: 15/817,881

(22) Filed: Nov. 20, 2017

(65) Prior Publication Data

US 2018/0200304 A1    Jul. 19, 2018

Related U.S. Application Data

(62) Division of application No. 14/151,766, filed on Jan. 9, 2014, now abandoned.

(60) Provisional application No. 61/751,051, filed on Jan. 10, 2013.

(51) Int. Cl.
*A61K 35/33* (2015.01)
*C12N 5/077* (2010.01)

(52) U.S. Cl.
CPC ............ *A61K 35/33* (2013.01); *C12N 5/0656* (2013.01)

(58) Field of Classification Search
CPC .............................. C12N 5/0656; A61K 35/33
See application file for complete search history.

(56) References Cited

U.S. PATENT DOCUMENTS

| 7,964,751 | B2 | 6/2011 | Herzig et al. |
| 8,987,263 | B2 | 3/2015 | Shinitzky et al. |
| 2013/0131009 | A1* | 5/2013 | Gorbunova ......... C08B 37/0072 435/352 |
| 2015/0157588 | A1 | 6/2015 | Cohen et al. |
| 2019/0201439 | A1* | 7/2019 | Naughton .............. A61K 35/54 |

FOREIGN PATENT DOCUMENTS

| WO | 2011119805 | 9/2011 | |
| WO | WO-2011119805 A2 * | 9/2011 | .............. C12P 19/26 |

OTHER PUBLICATIONS

Gorbunova et al., "Cancer resistance in the blind mole rat is mediated by concerted necrotic cell death mechanism", Nov. 20, 2012, Proceedings of the National Academy of Sciences of the United States of America vol. 109(47), p. 19392-19396.*
Gnecchi et al., "Bone Marrow-Derived Mesenchymal Stem Cells: Isolation, Expansion, Characterization, Viral Transduction, and Production of Conditioned Medium", 2009, Humana Press, Stem Cells in Regeneratiive Medicine: Methods and Protocols Ch. 18, p. 281-293.*
Mamchur et al., "Adipose-Derived Stem Cells of Blind Mole Rat Spalax Exhibit Reduced Homing Ability: Molecular Mechanisms and Potential Role in Cancer Suppression", epub Jul. 13, 2018, Stem Cells 36, p. 1630-1642.*
Karin M., Inflammation and cancer the long reach of RAS, Nature Medicine, 11:20-21 (2005).
Seluanov et al., Hypersensitivity to contact inhibition provides a clue to cancer resistance of naked mole-rat, PNAS, 106(46):19352-19357 (2009).

* cited by examiner

*Primary Examiner* — Maria G Leavitt
(74) *Attorney, Agent, or Firm* — Browdy and Neimark, PLLC (57) ABSTRACT

A conditioned cell culture medium of cells derived from *Spalax* or naked mole rat (*Heterocephalus glaber*) and methods for preparing it are provided. Pharmaceutical compositions comprising the conditioned cell culture medium and its use in the treatment of cancer as well as methods for identifying anti-cancer agents are also provided.

5 Claims, 5 Drawing Sheets

SPALAX FIBROBLAST-DERIVED ANTI-CANCER AGENTS

The present invention is in the field of cancer treatment and in particular to compositions comprising *Spalax* derived anti-cancer agents.

BACKGROUND INFORMATION

Cancer is one of the leading causes of death in the world. Notwithstanding steady progress in the understanding of this multifaceted disease, many cancers still are not treatable. Laboratory mice and rats provided invaluable knowledge in biomedical research and pharmaceutics; however, these animals were subjected to inbreeding and artificial selection for the experiments' standardization purposes, which ultimately caused loss of stress tolerance and naturally selected features.

Throughout the last forty years, several thousand *Spalax* individuals have been housed and studied in the Animal Facility at the Institute of Evolution of Haifa University. Despite this small rodent's (~100-200 gr.) extremely long lifespan (>20 years), none of the animals have ever developed spontaneous tumors, nor do they show any aging-related phenotypic changes. The mole rat, *Spalax ehrenbergi*, is a wild, solitary rodent of the Eastern Mediterranean region. *Spalax* inhabits a system of poorly ventilated dark, sealed underground tunnels protected from climatic extremes, pathogens, and predation. During the Mediterranean rainy season animals are engaged in intensive digging under extreme hypoxic conditions. *Spalax* has evolved a unique adaptive complex for living underground, including a unique ability to cope with extreme hypoxia and hypercapnia (Nevo et al. 2001). *Spalax* can conduct intensive aerobic work under low $O_2$ pressures (down to 3% $O_2$) due to increased muscular mass, high density of blood vessels and mitochondria resulting in reduced oxygen diffusion distance and efficient oxygen delivery even at low capillary $PO_2$ (Nevo et al. 2001; Shams et al. 2005a). Hypoxia can result in a failure to maintain essential cellular functions and contributes to cardio- and cerebrovascular failure, pulmonary diseases and cancer, which together are the primary sources of morbidity in the western world. *Spalax* genes exhibit hypoxia-related adaptations in structure and function (Shams et al. 2005b; Ravid et al. 2007; Avivi et al. 2010; Schulke et al. 2012). Noteworthy are *VEGF*, constitutively highly expressed as compared to rats (Avivi et al. 2005); p53 that harbors mutations in the DNA-binding site, identical to the most common p53 mutations in tumors, however, in *Spalax* renders bias against apoptosis but favors cell cycle arrest/DNA repair both in vitro and in vivo (Avivi et al, 2007); and a unique *Spalax* heparanase splice variant that was shown to decrease tumor size by a factor of 7 as well as reduced metastatic activity compared to native heparanase (Nasser et al. 2009). Furthermore, assessment of *Spalax* transcriptome assembly data has revealed enrichment of genes that overlap cancer-resistance, apoptosis, angiogenesis pathways and hypoxia-tolerance (Malik et al. 2011; Malik et al. 2012). This provides evidence that *Spalax* are extraordinarily highly resistant to malignant transformation. Elucidating the mechanisms employed by this wild non inbred, naturally cancer-resistant *Spalax* has great importance as early curing and preventative measures may be the most efficient way of dealing with increased cancer rates. It is an object of the present invention to provide anti-cancer agents based on the intrinsic mechanisms of *Spalax* and related species.

SUMMARY OF THE INVENTION

The present invention relates, in one aspect, to a conditioned cell culture medium of cells derived from *Spalax* or naked mole rat (*Heterocephalus glaber*), or a biologically active fraction thereof.

In another aspect, the present invention provides a method for identifying an anti-cancer agent, comprising: (a) obtaining a conditioned cell culture medium of cells as defined herein below; (b) fractionating said conditioned cell culture medium, thereby obtaining fractions; (c) contacting cancer cells and normal cells with said fractions of (b), and identifying active fractions that kill or inhibit the proliferation of Cancer cells but have no or little effect on proliferation of normal cells; and (d) collecting said active fractions of (c) and optionally repeating step (c) until one or more anti-cancer agent(s) are identified.

In an additional aspect the present invention is directed to a method for producing a conditioned cell culture medium of cells derived from *Spalax* naked mole rat (*Heterocephalus glaber*), comprising: (a) obtaining *Spalax* or naked mole rat fibroblasts; (b) culturing said *Spalax* or naked mole rat fibroblasts in a growth medium, thereby producing a *Spalax* or naked mole rat fibroblast-conditioned composition and (c) collecting said *Spalax* or naked mole rat fibroblast conditioned composition.

In still another aspect, the present invention provides an active agent selected from: (i) a conditioned cell culture medium of cells derived from *Spalax* or naked mole rat (*Heterocephalus glaber*); (ii) a biologically active fraction of (i); or (ii) a pharmaceutical composition comprising (i) or (ii) and a pharmaceutically active carrier, excipient or diluent.

In yet another aspect, the present invention relates to a method for treatment of cancer or inhibiting cancer metastasis in a subject diagnosed with cancer, said method comprising administering to said subject an effective amount of the active agent of the present invention.

In still and additional aspect, the present invention provides a method for killing cancer cells, inhibiting proliferation of cancer cells or inhibiting cancer cell migration, comprising administering to a subject in need thereof an effective amount of the active agent of the present invention.

In yet an additional aspect, the present invention provides a pharmaceutical composition comprising a pharmaceutically acceptable carrier, excipient or diluent and the active agent of the present invention.

BRIEF DESCRIPTION OF THE DRAWINGS

FIG. 1A and FIG. 1B show the effect of DMB/TPA application on skin cancer induction in *Spalax* and mice: Representative images showing macroscopic and microscopic skin changes in *Spalax* (FIG. 1A) and (FIG. 1B). (FIG. 1A) Normal pre-treatment tissues (left image. Extensive necrosis of skin and subcutaneous adipose tissue were found after 10 days (middle image). Completely healed skin lesion showing epidermal thickening with hyperkeratosis and prominent dermal fibrosis (right image). Hematoxylin and eosin staining, ×40 (left and middle images) and ×100 (right images). (FIG. 1B) Normal pretreatment tissues (left images), Intra-epidermal blisters, partially ruptured with erosion formation and crusting, congestion, and inflammatory cell infiltrate within the dermis indicate ongoing inflammation (middle image. Skin papillary outgrowths with thickened, dysplastic epidermis, numerous mitoses and foci suggestive of invasive squamous cell carcinoma Hematoxylin and eosin staining, ×40 (right images).

FIG. 2 depicts the effect of 3-Methylcholanten treatment on soft tissue tumor induction in *Spalax* and mice. Animals were treated with a single injection of 3MCA as follows: 200 μg/200 μL for mice; 1 mg/500 μL for *Spalax*. Animals were observed once a week until development of pathological process, (tumors could be palpated), and then 2-3 times a week. Animals were sacrificed, issues were removed, and either immediately frozen in Liquid-$N_2$ and kept at −80° C., or fixed in paraformaldehyde. Representative images show macroscopic and microscopic observations. Mouse: An ill-defined, soft mass, with foci of necrosis and hemorrhage; diagnosed as high-grade fibrosarcoma by histology. *Spalax*: a well-circumscribed, firm, whitish nodule composed of benign spindle cells organized into long regular bundles-benign fibrosis.

FIG. 3A-FIG. 3D depict 3MCA-induced fibrosarcoma in *Spalax*. (FIG. 3A) Pathologic specimen, toluidine blue staining. Note spindle shaped cells; nuclei are variable in shape, size and chromatin distribution. Nucleoli vary in frequency. Giant cells are present. (FIG. 3B) Transmission electron microscopy (TEM): Dilated, elongated rough endoplasmic reticulum (black arrow) and collagen fibers (white arrow) (FIG. 3C) TEM: giant, monstrous nucleus (N).

FIG. 4 shows effect of co-culture of fibroblasts with Hep3B cancer cells. *Spalax* fibroblasts kill co-cultured cancer cells. Hep3B cells (TC) were cultured in Roswell Park Memorial Institute medium (RPMI)/Dulbecco's Modified Eagle Medium: Nutrient Mixture F-12 (DMEM-F12) (1:1) supplemented with 15% fetal bovine serum (FBS) alone (left column, or co-cultured with mouse newborn normal fibroblasts (MF) (middle column), and with *Spalax* newborn normal fibroblasts (right column). Fibroblasts were plated first ($5×10^4$, in 6-well plates), and cancer cells were added within 1 h ($5×10^3$), with a 10:1 fibroblasts-to-cancer cell ratio. In parallel, control cultures of cancer cells and fibroblasts were plated with the same number of cells separately. White arrows point to the foci of destroyed cancer cells, and black arrows show the fibroblast-tumor cell colony boundaries. Cells in mono- and co-cultures were observed and photographed daily. Representative images of eight plated for each sample at different time intervals are shown. Magnification ×200.

FIG. 6A-FIG. 6F shows suppressing effects of *Spalax* fibroblasts conditioned media on different cancer cells of various origins. (FIG. 6B) *Spalax* fibrosarcoma cells (SpFS2240) were incubated for 3 or 7 days in full medium or under conditioned medium (CM) of *Spalax* adult skin normal fibroblasts (SpSNF CM), Hep3B (Hep3B CM), *Spalax* fibrosarcoma (SpFS2240 CM). Cell viability was evaluated by using PRESTO BLUE® reagent. Results are presented as percentage of control (SpFS2240 CM), mean±S.D. (FIG. 6C) MCF7 ($5×10^3$ cells) were grown in soft agar on top of a monolayer of mouse newborn (MNbF), or *Spalax* newborn (SpNbF) fibroblasts in 35-mm culture dishes. Dishes were incubated until cell colonies were well defined. Colonies were stained with 0.05% crystal violet solution and counted under light microscope after 5 and 11 days in soft agar. (FIG. 6D and FIG. 6E) Hep3B cells ($1×10^4$ cell/well) were culture in 6-well plates under conditioned medium of *Spalax* adult skin fibroblasts (FIG. 6D) or grown in medium generated by Hep3B cells (FIG. 6E). After 9 days cells were collected, and their survival rates were assessed by trypan blue extrusion assay and analyzed by using an automatic cell counter (COUNTESS®, Life Technologies). Viable and dead cell size and numbers are presented in black and white columns, respectively.

DETAILED DESCRIPTION OF THE INVENTION

It has been found in accordance with the present invention that *Spalax* is resistant to two-stage DMBA/TPA, and 3-MCA carcinogens (Manov et al. 2013). DMBA/TPA is commonly used to study malignant transformation resembling formation of human squamous cell carcinoma (Yuspa 1998). In a single dose, DMBA has been shown to induce substantial oxidative stress (Izzotti et al. 1999), followed by repetitive application of TPA that cause persistent inflammation supporting tumorigenesis (Goerttler et al. 1984). Example 1 herein below shows that mice treated by DMBA/TPA initially developed benign papillomas, which subsequently transformed to squamous cell carcinomas. In contrast, treatment of *Spalax* led to necrotic wounds which completely healed with no signs of malignancy. The carcinogen 3-MCA is known to produce primary skin fibrosarcoma through persistent inflammation leading to DNA-adducts (Krelin et al. 2007). 3-MCA is metabolized via P450 enzymes to form a reactive metabolite causing severe oxidative damage (Flesher et al. 1998). In our study, 100% of 3-MCA-injected mice and rats developed tumors at the injection site within 2-3 and 4-6 months, respectively. Following the first year of treatment no *Spalax* animals showed any pathological process. However two individuals out of eight developed benign fibrotic overgrowth after 14 and 16 months respectively, and only one case of malignant transformation in a >10 years-old *Spalax* animal was recognized, 18 mouth after 3-MCA injection.

The present inventors developed a co-culture system involving normal primary fibroblasts isolated from different rodent species (*Spalax*, naked mole rat *Heterocephalus glaber*, mouse, and spiny mice *Acomys cahirinus*), with human hepatocellular and breast carcinomas (Hep3B and MCF7 cells), as well as *Spalax*-derived fibrosarcoma cells (SpFS2240). It has been found in accordance with the present invention (Example 2) that both *Spalax* and *Heterocephalus* fibroblasts restrict malignant behavior either through direct fibroblast-cancer cell interaction or via soluble factors secreted by normal *Spalax* fibroblasts into conditioned medium.

The present invention thus relates, in one aspect, to isolated fibroblasts derived from *Spalax* or naked mole rat (*Heterocephalus glaber*) for use in producing a *Spalax* fibroblast-conditioned composition or naked mole rat fibroblast-conditioned composition.

In another aspect, the present invention provides a conditioned cell culture medium of cells derived from *Spalax* or naked mole rat (*Heterocephalus glaber*), or a biologically active fraction thereof.

The term "conditioned medium" in general refers to a growth medium in which cells have been cultured/incubated for a period of time followed by harvest of such medium from the cultured cells. A conditioned medium contains metabolites, growth factors, and extracellular matrix proteins secreted into the medium by the cultured cells.

In accordance with the present invention, the terra "conditioned medium of cells derived from *Spalax* or naked mole rat (*Heterocephalus glaber*)" refers to the medium harvested from the cultured cells that were originally isolated from these animals. The conditioned medium may foe derived from a medium suitable for culture of *Spalax* or naked mole rat cells such as, but not limited to, DMEM-F12 medium, and may contain additional nutrients. The suitable culture medium is easily identified by culturing the cells in the desired medium and identifying healthy propagation or absence of senescence of the cells. The terms "*Spalax* cell-conditioned composition" and "naked mole rat cell-conditioned composition" are used interchangeably herein with the terms "conditioned medium of cells derived from *Spalax*" and "conditioned medium of cells derived from naked mole rat (*Heterocephalus glaber*)", respectively.

Thus, in certain embodiments, the cells are derived from *Nannospalax ehrenbergi* (*Spalax ehrenbergi*). In certain embodiments the cells are selected from the group consisting of adipocytes, lymphatic cell, endothelial cells, hepatocytes and intestinal cells, kidney epithelial cells, placental epithelial and endothelial cells, and in particular, the cells are skin or lung fibroblasts.

In certain embodiments, the cells, such as the fibroblasts, are primary cells, i.e., they are harvested from living animals and cultured until they stop dividing and senesce.

In certain embodiments, the fibroblasts form an immortalized cell line.

As used herein, the term "a biologically active fraction thereof" refers to a fraction of the conditioned cell culture medium of cells derived from *Spalax* or naked mole rat obtained by fractionation of the conditioned medium and shown to retain the same biological activities as shown herein for the whole conditioned medium such as cytotoxic or anti-metastatic activity. Conveniently, the biological activity may be determined using a xenograft, e.g., but not limited to transplantation of human cancer cells in a mouse, or in vitro by utilizing culture wells and cell attachment substrates, such as, but not limited to, porous membranes (such as TRANSWELL®, Corning Inc.), that allow observation of cell migration in the presence or absence of certain cells or active agents. The fractionation of the conditioned medium may be carried out by standard procedures, e.g., organic extractions, size exclusion fractions and/or reverse phase chromatography carried out using e.g., high pressure liquid chromatography (HPLC) columns and pumps, as knows in the art.

In another aspect the present invention provides a method for identifying at least one anti-cancer agent, comprising: (a) obtaining a conditioned cell culture medium of cells as defined herein above; (b) fractionating said conditioned cell culture medium, thereby obtaining fractions; (c) contacting cancer cells and normal cells with said fractions of (b), and identifying active fractions that kill or inhibit the proliferation of cancer cells but have no or little effect on proliferation of normal cells; and (d) collecting said active fractions of (c) and optionally repeating step (c) until one or more anti-cancer agent(s) are identified.

The optional step of repeating step (c) refers to the repeated fractionation of fractions obtained in step (d) using other techniques in order to separate various compounds collected in the same fraction.

In certain embodiments, the cancer and normal cells used in the method for identifying the at least one anti-cancer agent are human cells, which may be epithelial cells and mesenchymal cells, respectively.

In an additional aspect, the present invention is directed to a method for producing a conditioned cell culture medium of cells derived from *Spalax* or naked mole rat (*Heterocephalus glaber*), comprising: (a) obtaining *Spalax* or naked mole rat cells; (b) culturing said *Spalax* or naked mole rat cells in a growth medium, thereby producing a *Spalax* or naked mole rat cell-conditioned composition; and (c) collecting said *Spalax* or naked mole rat cell-conditioned composition.

In certain embodiments, the cells utilized for making the *Spalax* or naked mole rat cell-conditioned composition are selected from the group consisting of adipocytes, lymphatic cells, endothelial cells, hepatocytes and intestinal cells, kidney epithelial cells, placental epithelial and endothelial cells, and in particular, the cells are skin or lung fibroblasts.

The procedure for obtaining *Spalax* or naked mole rat cells is well-known in the art and may involve partial digestion of animal tissues by collagenase, followed by multiple washing procedures by using culture media supplemented with fetal bovine serum, and plating in tissue culture plates containing antibiotic and antimycotic agents. The conditioned medium may be derived from a medium suitable for culture of *Spalax* or naked mole rat cells such as, but not limited to, DMEM-F12 medium, and may contain additional nutrients. The collection of the conditioned medium may be done by, for example, but not limited to, centrifugation of the cells and the collection of the supernatant or by filtering the cells and collecting the filtrate.

In still another aspect, the present invention provides an active agent selected from: (i) a conditioned cell culture medium of cells derived from *Spalax* or naked mole rat (*Heterocephalus glaber*); (ii) a biologically active fraction of (i); or (iii) a pharmaceutical composition comprising (i) or (ii) and a pharmaceutically active carrier, excipient or diluent.

In yet another aspect, the present invention relates to a method for treatment of cancer or inhibiting cancer metastasis in a subject diagnosed with cancer, said method comprising administering to said subject an effective amount of the active agent of the present invention.

In still an additional aspect, the present invention provides a method for killing cancer cells, inhibiting proliferation of cancer cells or inhibiting cancer cell migration, comprising administering to a subject in need thereof an effective amount of the present invention.

The term "treating" or "treatment" as used herein includes abrogating, substantially inhibiting, slowing or reversing the progression of a condition, substantially ameliorating clinical symptoms of a condition or substantially preventing the appearance of clinical symptoms of a condition. With regard to cancer, the term refers to preventing or delaying cancer, inhibiting tumor growth or causing death of cancer cells, including primary and metastatic cancer cells. Such treatment can also lead to regression of tumor growth, i.e., to decrease in size or complete regression of the tumor, and to elimination of metastases. The terms "tumor" and "cancer" are used interchangeably herein.

In certain embodiments, the cancer cells are selected from the group consisting of carcinoma cells, sarcoma cells, glioma cells, leukemia cells and lymphoma cells. In particular, the carcinoma cells may be selected from the group consisting of breast cancer carcinoma cells, hepatocellular carcinoma cells and breast adenocarcinoma cells.

In some embodiments of the invention, the treatment of cancer comprises inhibiting cancer metastasis.

In yet an additional aspect, the present invention provides a pharmaceutical composition comprising a pharmaceutically acceptable carrier, excipient or diluent and the active agent of the present invention.

Optionally, the active agents or compositions of the invention may be administered to the subject in combination (concurrently or sequentially) with other anti-cancer agents or treatments. For example, they may be administered in combination with one or more chemotherapeutic agents such as, but not limited to, alkylating agents, e.g., Cyclophosphamide, Ifosphamide, Melphalan, Chlorambucil, Carmustine (BCNU, Gliadel), Lomustine (CCNU), Decarbazine, Procarbazine, Busulfan, and Thiotepa; antimetabolites, e.g. Methotrexate, 5-Fluorouracil, Cytarabine, Gemcitabine, 6-mercaptopurine, 6-thioguanine, Fludarabine, and Cladribine; anthracyclins, e.g., daunorubicin. Doxorubicin, Idarubicin, Epirubicin and Mitoxantrone; camptothecins, e.g., irinotecan and topotecan; taxanes, e.g., paclitaxel and docetaxel; and platinums, e.g., Cisplatin, carboplatin, and Oxaliplatin, as well as to immunotherapies, e.g., Herceptin and Cetuximab, hormone responsive therapies, e.g., Tamoxifen, Raloxifene, Fulvestrant, Anastrozole, Letrozole or Exemestane for breast cancer, or anti-androgens, e.g., flutamide for prostate cancer, small molecules inhibiting epidermal growth factor receptor (EGFR, e.g., Lapatinib or gefitinib), anti-angiogenic therapy, e.g., Bevacizumab, sunitinib, sorafenib and pazopanib, antibodies and small molecules targeted against beta 1 integrins (e.g., ATN-161, Volociximab and JSM6427), or inhibitors, antagonists and small molecules against urokinase receptor (UPAR).

Advantageously, the compositions of the invention may be used in conjunction (concurrently or sequentially) with surgery or radiotherapy. For example, the active agent of the invention may be used concomitantly with, or within 1-4 days of a surgical treatment for cancer. Dissemination of tumor cells, which are the source for the progression to metastatic disease, may occur as a result of the surgical operation. By performing such procedures in conjunction with the compositions of the invention, cancer metastasis may be prevented or inhibited. Thus the compositions and methods of the invention may be used to inhibit post-surgery metastatic process.

Given that dissemination of tumor cells may have already occurred even at an early stage of tumor progression, the anti-cancer agents or treatments that may be administered in combination with the compositions of the invention, include, in some embodiments, neoadjuvant treatment, namely radiotherapy, chemotherapy, hormone therapy and/or immunotherapy used for shrinking the size of the tumor prior to surgical operation.

The active agent of the present invention or fractions thereof can be administered to individuals in need per se or in a pharmaceutical composition with suitable carriers, excipients or diluents.

The term "pharmaceutically acceptable carrier" refers to a carrier or diluent that does not cause irritation or other adverse effect to an organism and does not have an adverse effect on the biological activity and properties of the administered compound. The "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active agents into preparations that can be used pharmaceutically. Proper formulation is dependent upon the route of administration chosen.

Suitable routes of administration may, for example, include oral, rectal, transmucosal, especially transnasal, intestinal, or parenteral delivery, including intramuscular, subcutaneous and intramedullary injections as well as intrathecal, direct intraventricular, intravenous, intraperitoneal, intranasal or intraocular injections.

Alternatively, the pharmaceutical composition may be administered in a local rather than systemic manner, for example, via injection directly into a tissue region of a patient.

For injection, the active ingredients of the compositions of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example DMSO, or polyethylene glycol are generally known in the art.

Pharmaceutical compositions suitable for use in context of the present invention include compositions wherein the active ingredients are contained in an amount effective to achieve the intended purpose. More specifically, a "therapeutically effective amount" means an amount of an active ingredient effective to prevent, alleviate or ameliorate symptoms of a disease or disorder or prolong the survival of the subject being treated.

Determination of a therapeutically effective amount is well within the capability of those skilled in the art, especially in light of the detailed disclosure provided herein.

Depending on the severity and responsiveness of the condition to be treated, dosing can be of a single or a plurality of administrations or a single administration of a slow release composition, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

The present invention further encompasses an isolated *Spalax* cancer cell line. In certain embodiments, the isolated *Spalax* cancer cell line is established from *Spalax* fibrosarcoma, in particular it may be established from *Spalax ehrenbergi* (*Nannospalax*) fibrosarcoma, for example, as in the specific case described herein below in Example 1, it may be a isolated *Spalax* cancer cell line designated SpFS2240.

The present invention will now be described in more detail in the following non-limiting Examples and the accompanying figures.

EXAMPLES

Materials and Methods

Animals: Blind mole-rat (*Spalax*) spiny mice (*Acomys cahirinus*), rats (*Rattus norvegicus*), and C57BL/6 mice were subjected to DMBA/TPA or 3MCA treatments. For DMBA/TPA treatment, eight *Spalax* and six mice individuals were used. For 3MCA treatment 12 *Spalax*, six mice, and six rats were used.

DMBA/TPA treatment: A single application of 200 µg of DMBA dissolved in 100 µL of acetone for mice, and 500 µg in 250 µL for *Spalax* were used. Three days thereafter, mice and *Spalax* were treated with 30- or 60 µg of TPA dissolved in 100- or 250 µL of acetone, respectively, three times per week for 2-3 months, until all mice developed advanced cancer and were subsequently sacrificed. *Spalax* continued to be treated for an additional three months.

3-MCA carcinogen treatment: Animals were treated with a single subcutaneous injection of 3MCA dissolved in olive oil in the upper back as follows: 200 µg/200 µL for mice; 1 mg/500 µL for *Spalax*; and 1.5 mg/500 µL for rats (according to average body weight).

Cell culture: Primary fibroblasts were isolated from skin and lungs of *Spalax*, naked mole rat, mice, and *Acomys* as described in *SI* (*Materials and Methods*). Human cancer cell lines Hep3B or MCF7 were co-cultured with fibroblasts and growth dynamics and interactions were investigated. Conditioned medium approaches and soft agar colony formation were employed to study the effects of soluble factors from *Spalax*, mice, and *Acomys* fibroblasts on cancer cell proliferation.

Light microscopy and Transmission electron microscopy. For histological examination the samples were fixed in paraformaldehyde, dehydrated, and embedded in paraffin. Sections were routinely stained with hematoxylin and eosin for pathological examination. For transmission electron microscopy specimens were prepared as previously described (Manov et al. 2011).

Cell cycle analysts. The cell cycle distribution was assessed by flow cytometry of propidium iodide (PI)-stained nuclei.

Supplementary Information

Detailed Materials and Methods

Animals: *Spalax*, spiny mice (*Acomys cahirinus*), rats (*Rattus norvegicus*) and C57BL/6 mice were tested. *Spalax* and *Acomys* were captured in the field and housed under ambient conditions in individual cages in the Animal Facility of the Institute of Evolution, University of Haifa. Noteworthy, *Spalax* do not undergo uniform acclimatization upon transfer from their natural habitat to a standardized laboratory environment but rather behave differentially according to their eco-geographic origins (Nevo 1999). The C57BL/6 mice were purchased from Harlan Laboratories (Jerusalem, Israel). Rats were supplied by the Animal House of the Psychology Department of Haifa University. All animals were kept with free access to food and water at 21-23° C. in a 12:12 light-dark cycle. All animals used for experiments were healthy. Animals were sacrificed with an inhalation anesthesia agent (isofluorane) overdose. All animal experiments were approved by the Institutional Ethics Committee.

DMBA/TPA treatment: Four *Spalax* individuals of 2 year old and 4 individuals over 10 years old; and 6 individuals of C57BL/6 mice, 3-4 month old, were used in the 7,12-Dimethylbenz(a) anthracene/12-O-tetradecanoylphorbol-13-acetate (DMBA/TPA) experiments. A single application of 200 µg of DMBA (Sigma Aldrich, Inc.) dissolved in 100 µL of acetone for mice, and 500 µg of DMBA dissolved in 250 µL acetone for *Spalax* were used. The solution was applied onto the bare skin of the animal. Three days after the initial DMBA dose, mice were treated with 30 µg of TPA (Sigma Aldrich, Inc.) dissolved in 100 µL of acetone, and *Spalax* with 60 µg of TPA dissolved in 250 µL of acetone. TPA was applied 3 times per week for 2-3 months after which all mice were sacrificed upon skin carcinoma formation, and continued with *Spalax* for another 3 months twice a week.

3-MCA carcinogen treatment: 3-methylcholanthrene (3-MCA) has been commonly used for induction of tumors in rodents (Malins et al 2004). In this experimental system, mice and rats develop local fibrosarcomas in 2 to 4 months, respectively (Krelin et al. 2007) and can be palpated as early as 30 to 60 days following injection. The recommended amount in the literature of 3MCA (Sigma Aldrich, Inc.) treatment of mice is 200 µg dissolved in 200 µL of olive oil. We calculated the amount applied to rats and *Spalax* according to their average weight. Hence, animals were treated with a single injection of 3MCA as follows: 200 µg/200 µL for mice; 1 mg/500 µL for *Spalax*; and 1.5 mg/500 µL for rats. Animals used in this experiment were; six ~2 years old *Spalax* individuals; six 10 years or older *Spalax* individuals; six 3-4 months-old mice; and six 3 months old white rats.

Animals were observed once a week until tumors could be palpated, and then 2-3 times a week. Animals were sacrificed, tissues were removed, and either immediately frozen in Liquid-$N_2$ and kept at −80° C., or fixed in paraformaldehyde.

Cell culture: Primary *Spalax*, mice, and *Acomys* fibroblast cells were isolated from under arm skin and lungs as described (Glaysher & Cree 2011), and grown in DMEM-F12 medium (Biological Industries, Beit Haemeq Israel), supplemented with 15% fetal bovine serum (FBS). Human cancer cell lines Hep3B and MCF7 are commercially available, and were grown in RPMI (Hep3B) and DMEM (MCF7) supplemented with 10% FBS, L-glutamine, penicillin and streptomycin (Biological Industries, Beit Haerneq Israel). Cells were incubated in a humidified atmosphere of 5% $CO_2$ and 95% $O_2$ at 37° C. *Spalax*-derived fibrosarcoma cells were isolated from tumor developed after 3MCA injection. Tumor specimen was minced and treated with collagenase (1 mg/ml) under aseptic conditions to obtain a single-cell suspension, which was plated in cultures dishes in DMEM-F12 medium supplemented with 15% FBS and penicillin-streptomycin-amphotericin B solution. Cells were serially cultured more than 40 times.

Co-cultures of cancer cells and fibroblasts. Normal fibroblasts and human derived Hep3B cells were co-plated in 6-well plates in 2 ml of culture medium Roswell Park Memorial Institute medium (RPMI)/Dulbecco's Modified Eagle Medium: Nutrient Mixture F-12 (DMEM-F12) (1:1) supplemented with 15% fetal bovine serum (FBS) (1:1) (Biological Industries, Kibbutz Beit Haemeq, Israel). Fibroblasts were plated first ($5\times10^4$), and cancer cells were added within 1 h ($5\times10^3$), with a 10:1 fibroblast-to-cancer cell ratio. In parallel, cultures of cancer cells and fibroblasts were plated with the same number of cells. The medium was changed every 3 days. Fibroblast-cancer cell co-interactions were observed and photographed by using inverted microscopy.

Generation of conditioned medium (CM). Normal fibroblasts or cancer cells ($1\times10^6$ cells) were plated in 10-cm tissue culture dishes and cultured in full medium containing 10% FBS for 4 days, thereafter supernatants were collected and cells were removed by centrifugation. The cell-free CM was then diluted with fresh culture medium (1:1) and used for further experiments. To investigate the viability and proliferation rates of cancer cells exposed to CM, normal fibroblasts or control medium, we used PRESTO BLUE® dye reagent (Invitrogen), as described in (Manov et al. 2004), and trypan-blue standard treatment followed by cell count using an automatic cell counter (COUNTESS®, Life Technologies).

Soft agar colony formation assay was performed as described (Tyan et al. 2011). In brief, $2\times10^5$ fibroblasts were seeded in 35-mm culture dishes and cultured for 2-3 days to reach confluence. After washing with PBS, 1 ml of 0.5% agar in DMEM-F12 containing 2% FBS was added on top of fibroblasts to form a base layer. After the agar was solidified, $5\times10^5$ MCF7 cells were suspended in 1 ml of 0.35% agar in DMEM containing 5% FBS and then added into the dish to form a cancer cell layer. Colonies were stained with 0.05% crystal violet solution and counted under light microscope after 5 and 11 days.

Microscopy. For histological examination the samples were fixed in 4% paraformaldehyde dissolved in PBS, dehydrated in increasing concentrations of ethanol, and embedded in paraffin. Five-micrometer sections were cut from paraffin blocks and routinely stained with hematoxylin and eosin for pathological examination.

For transmission electron microscopy specimens were fixed in 2.5% glutaraldehyde in 0.1 M sodium cacodylate buffer (pH 7.2), postfixed with 2% $OsO_4$, dehydrated in ethanol series and embedded in epoxy resin. Semi-thin sections were stained with 1% toluidine blue. Ultrathin sections (60 nm) were cut with a diamond knife, placed on 300-mesh copper grids, stained with 1% uranyl acetate, and viewed and photographed with a Transmission Electron Microscope.

Cell cycle analysis: The cell cycle distribution was assessed by flow cytometry of propidium iodide (PI)-stained nuclei. Following incubation, cells were harvested by trypsin, combined with medium containing floating cells, washed with PBS and stained with hypotonic PI solution (PI 50 µg/ml in 0.1% sodium citrate and 0.1% Triton X-100). The PI fluorescence of individual nuclei was recorded by FACSaria (Becton Dickinson, NJ, USA). A total of 10,000 events were acquired and corrected for debris and aggregate population.

Example 1

Resistance of *Spalax* to Chemically-Induced Cancer

Figure 1A:
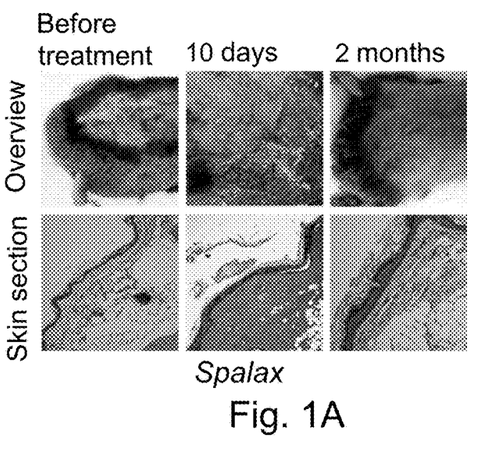
Figure 1B:
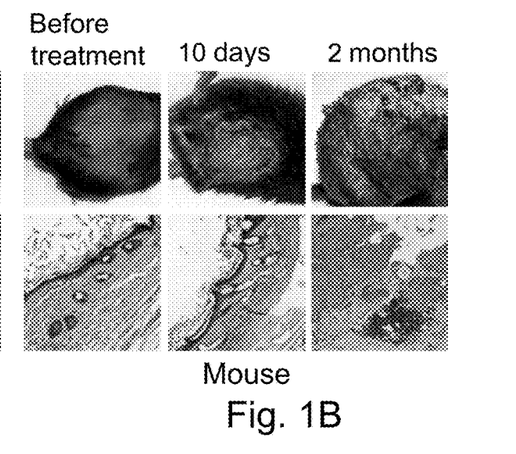

To assess experimentally if *Spalax* is resistant to chemically-induced carcinogenesis, we treated animals from different rodent species according to the following protocols:

DMBA/TPA treatment: *Spalax* and C57BL/6 mice were treated with DMBA/TPA to induce skin carcinogenesis (Goerttler et al. 1982). *Spalax* animals developed severe skin lesions within ten days (FIG. 1A, upper middle panel). Histological examination of hematoxylin and eosin stained tissue sections demonstrated extensive skin necrosis involving the deep parts of the dermis, massive infiltration of the affected areas with neutrophil leukocytes, and ulcerated epidermis locally covered with fibrino-purulent exudates (FIG. 1A, lower middle panel). The subcutaneous skeletal muscle and bone tissues were not affected, and no tumor was identified. The wounds completely healed within 7-9 weeks, resulting in epidermal thickening (FIG. 1A, right panels), and no further progression to skin tumors was observed, even though TPA treatments were extended to 6 months (November 2010-April 2011). In the control group, *Spalax* treated with acetone only did not show any changes in their skin macro- and microstructure, similar to non-treated animals (FIG. 1A, left panels). Following 7-10 days of DMBA/TPA treatment, mice demonstrated small intra-epidermal blisters; some of them ruptured forming superficial erosions with extensive crusting (FIG. 1B, middle panels), which subsequently underwent malignant transformation and development of multiple skin tumors within 2 months (FIG. 1B, upper right panel). Histological examination revealed papillary and flat epidermal outgrowths with prominent dysplastic features, similar to squamous cell carcinoma (FIG. 1B, right panels).

Figure 2:
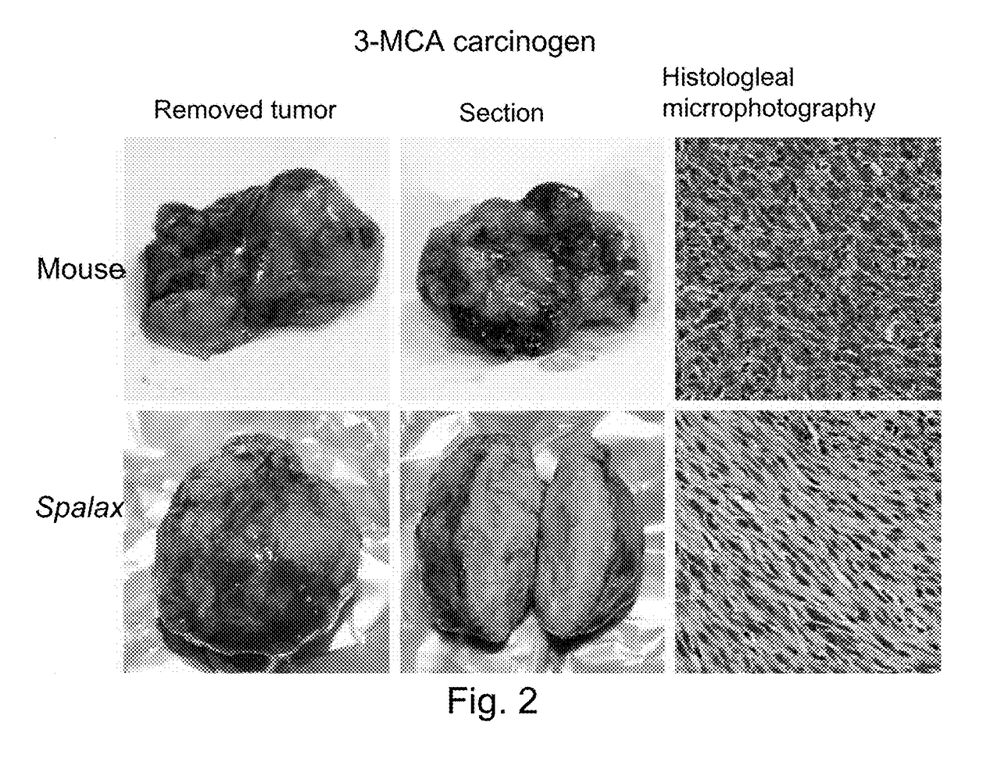
Figure 3A:
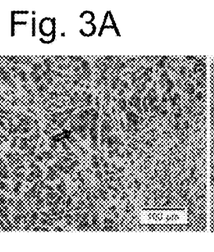
Figure 3B:
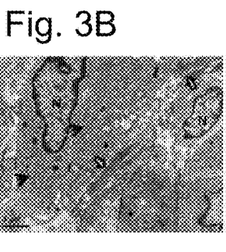
Figure 3C:
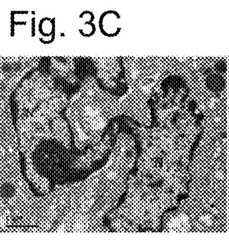
Figure 3D:
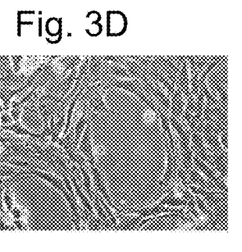
FIG. 3D Cell line established from *Spalax* fibrosarcomas phase contrast image after 6 months of continuous cultivation (×20).

3-MCA treatment: the ability of a single subcutaneous 3-MCA injection to induce fibrosarcoma is well documented (Krelin et al. 2007). The expected tumors appeared within 2-3 months in mice, and in 4-6 months in rats. Hypercellular spindle cell tumors with highly pleiomorphic, extensively proliferating cells (30 and more mitotic figures per 10 high power fields) arranged into intersected bundles or wide sheets were identified. Scant, partially myxoid stroma and areas of hemorrhagic necrosis were typical findings (FIG. 2, upper panel). While all examined tumors which bad been developed in 3-MCA-treated mice were qualified as high-grade fibrosarcomas, some of the rats presented lesions resembling low- to intermediate-grade fibrosarcoma. Importantly, *Spalax* did not show any pathological process for over a year. However, by 14 to 16 months following the 3-MCA. treatment, two of the *Spalax* animals (out of six old individuals and a total of twelve animals) developed a tissue overgrowth at the site of the injection. These lesions were well circumscribed in shape, unlike the ill-defined tumors found in mice (FIG. 2, lower panel). Histological examination revealed benign spindle cell proliferation most probably reflecting fibrosis at the site of incompletely resolved inflammatory reaction. Nonetheless, a single old *Spalax* individual developed 3-MCA-induced cancer 18 mouth after initial treatment (FIG. 3). A biopsy was performed, and the histological examination revealed a partially necrotic and heavily inflamed, spindle and epithelioid cell tumor with infiltrative borders and myxoid stroma. Cells demonstrated dyscohesion, polymorphism in size and shape (bizarre and giant cells present) and prominent nuclear atypia (FIG. 3A). This hypercellular tumor demonstrated high mitotic activity (above 30 mitoses per 10 high power fields) with abundant atypical mitotic figures. Transmission electron microscopy revealed fibrosarcoma-like findings (Antonescu & Baren 2004): deformed nuclei, some with monstrous appearance; long branching and dilated rough endoplasmic reticulum and abundance of extracellular collagen fibers (FIGS. 3B and 3C). Myofibroblastic differentiation was not observed. A cancer cell line was established from the tumor sample. Cells, able to attach and survive, showed a typical fibroblast phenotype (FIG. 3D). The morphology of isolated cells remained unchanged throughout a long culture time (40 passages, 8 months after isolation).

The remaining treated *Spalax* individuals showed no phenotypic or behavioral changes, and are still under observation in the Animal House over two years following treatment (October 2010-January 2013).

Example 2

*Spalax* Fibroblasts Suppress Growth of Cancer Cells In Vitro

Figure 4:
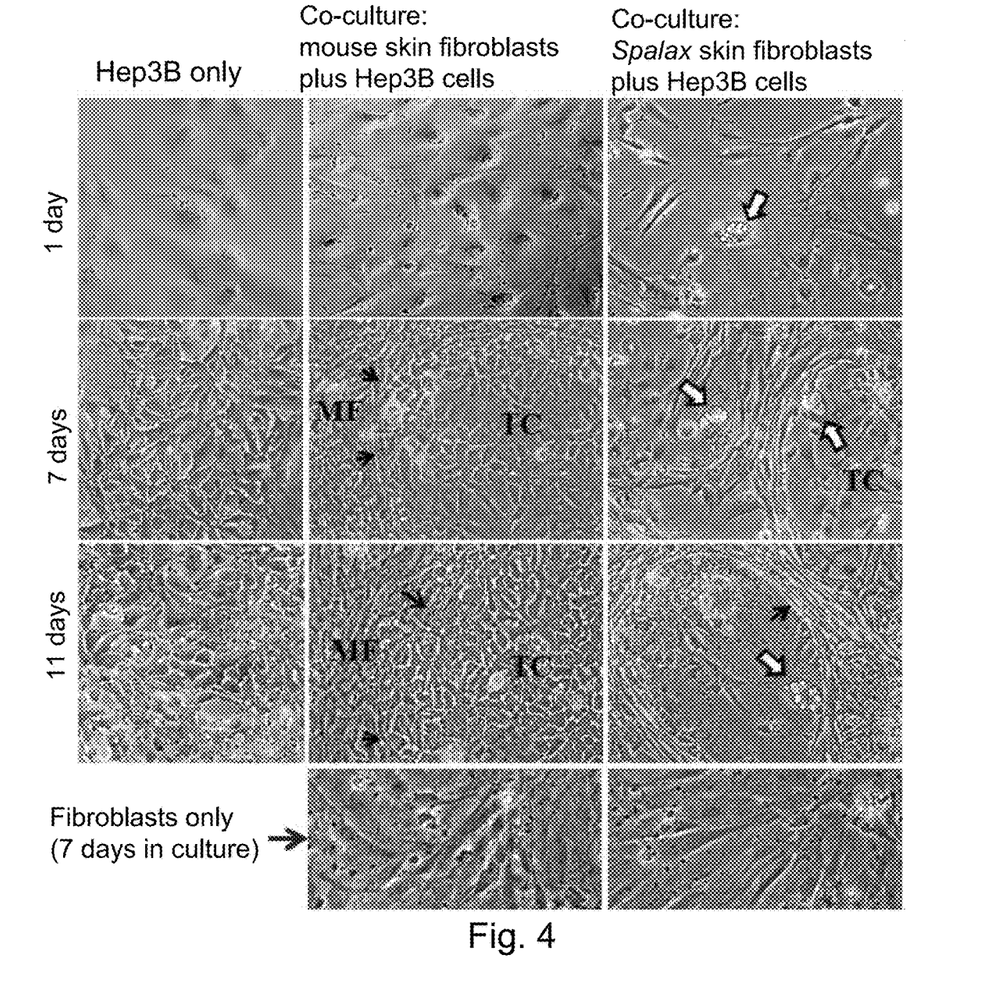

To compare the effects of *Spalax* and mouse fibroblasts on growth of human epithelial cancer (Hep3B), we used a co-culture approach, where skin fibroblasts isolated from newborn rodents were cultured together with cancer cells on a shared surface (FIG. 4). The number of cancer cells co-cultured with mouse fibroblasts increased gradually, and on Day 7, Hep3B cells surrounded by mouse fibroblasts reached ~80% confluence, similar to control (Hep3B only). In contrast obvious inhibition of cancer cell growth was found when. Hep3B cells were co-cultured with *Spalax* fibroblasts: foci of destroyed cancer cells were visible (FIG. 4). Prolonged co-cultivation up to 11 days resulted in further destruction of cancer cell colonies by *Spalax* fibroblasts and the spaces previously occupied by Hep3B cells were invaded by fibroblasts. Overgrown Hep3B colonies were found when co-cultured with mouse fibroblasts.

Figure 5:
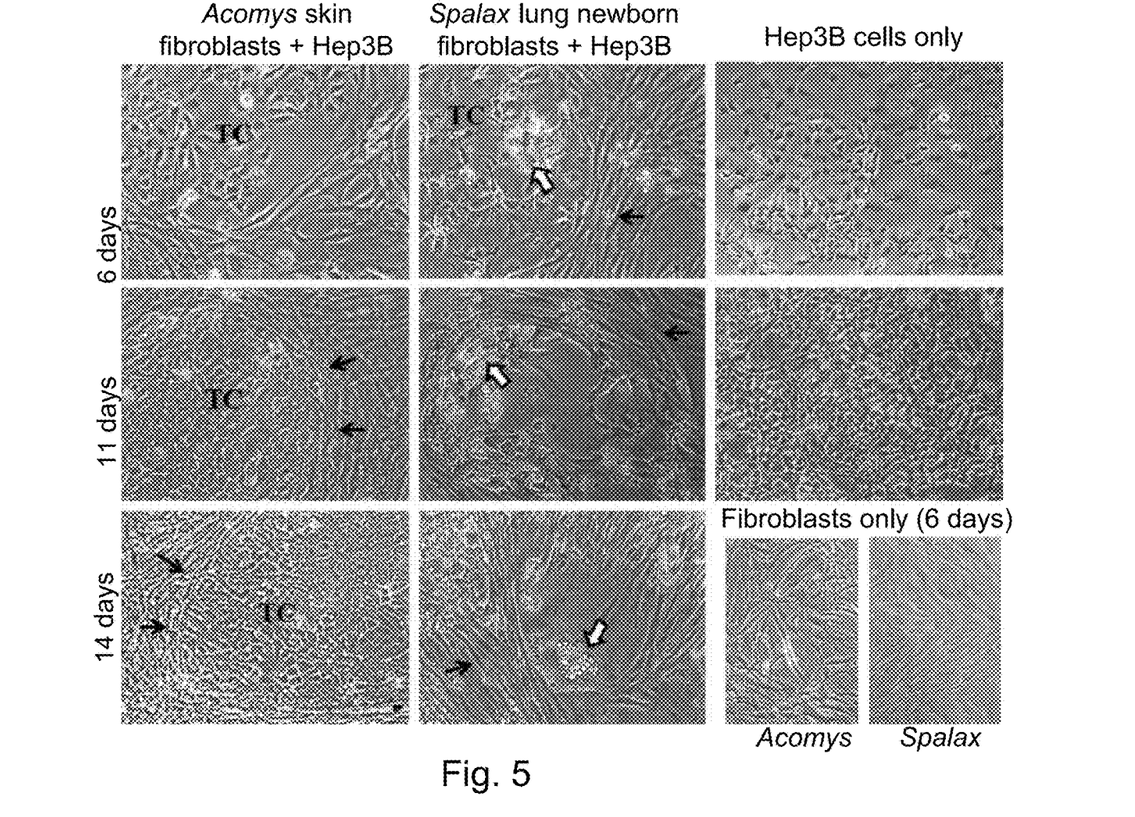
FIG. 5 shows the effects of *Spalax* lung and *Acomys* skin fibroblasts on growth of co-cultured human hepatoma cells (Hep3B). Cancer cells were cultured either alone or in presence of *Acomys* and *Spalax* lung fibroblasts in the ratio of 1:10 ($5×10^4$ fibroblasts and $5×10^3$ cancer cells in 6-well plates) in RPMI/DMEM-F12 media (1:1) containing 10% FBS. The phase contrasts images (×200) represent cells interactions after 6, 11, and 14 co-culturing days. Black arrows point to fibroblasts surrounding cancer cells colonies. White arrows show foci of dead cancer cells.

Since we compare a wild mammal with laboratory animals that could be sensitive to cancer, we conducted a series of experiments using skin fibroblasts isolated from *Acomys*, which like *Spalax*, is a wild rodent, however with a short life span. As shown in FIG. 5, no inhibitory effect was found when *Acomys* fibroblasts were co-cultured with Hep3B cells. On the contrary, co-culture with *Acomys* fibroblasts promoted cancer cell invasion similar to mouse fibroblasts.

Next, we studied the cancer-suppressing ability of *Spalax* fibroblasts isolated from lung tissues of newborn animals, to confirm that cancer inhibition is not limited to skin fibroblasts (FIG. 5). Hep3B colonies were similarly inhibited and destroyed when co-cultured with *Spalax* lung fibroblasts.

Figure 6A:
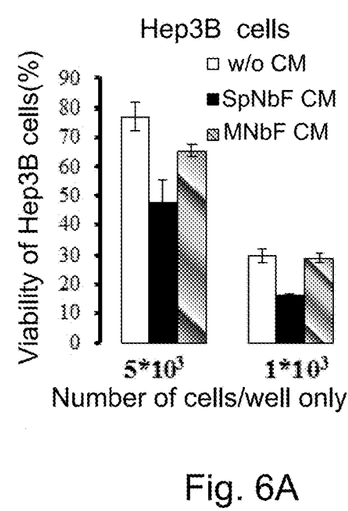
(FIG. 6A) Hep3B cells were seeded in a 96-well plate at a density $5×10^3$ and $1×10^3$ cells well in RPMI-DMEM/F12 culture medium supplemented with 10% FBS, conditioned with *Spalax* or mouse skin newborn fibroblasts or no fibroblast control. Hep3B cells were incubated for 4 days; levels of proliferation were estimated by PRESTO BLUE® Reagent. Results are presented as percentage of control, mean±S.D.
Figure 6B:
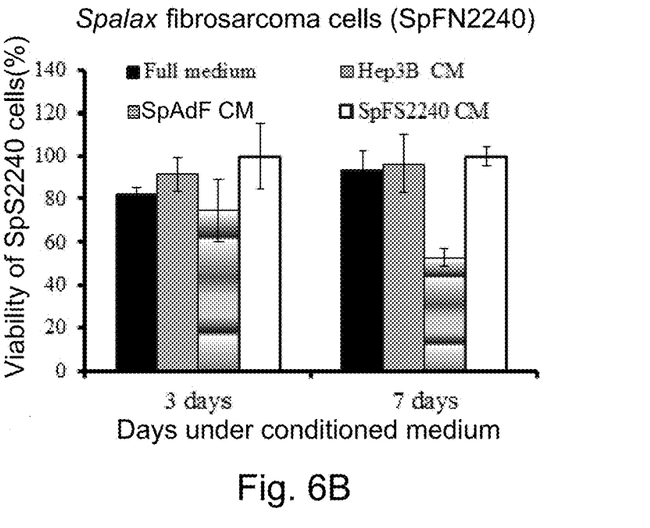
Figures 6C, 6D:
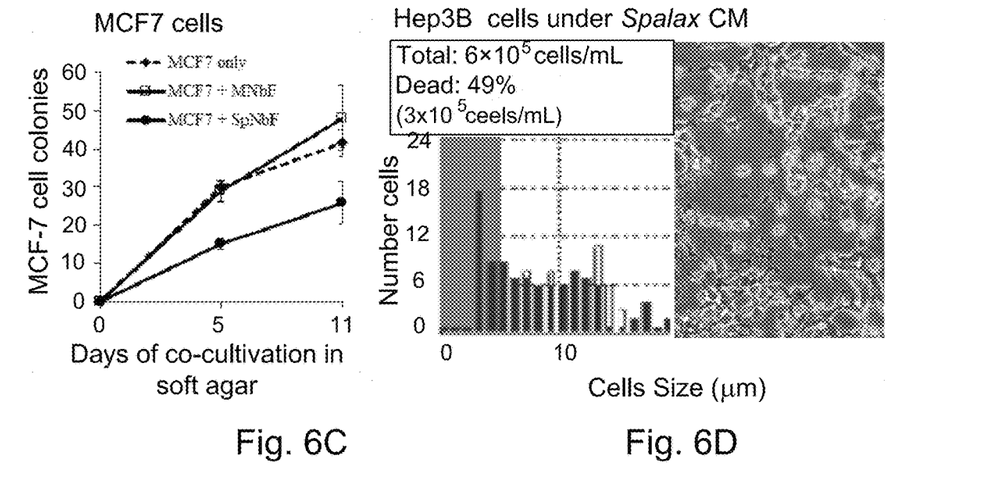

To determine whether the anti-cancer activity of *Spalax* fibroblasts was mediated by fibroblast-secreted soluble factors, conditioned medium and soft agar colony formation approaches were used. Cancer cells of different origins were incubated under conditioned media of normal fibroblasts, which had not been previously exposed to cancer cells or other stimuli. As demonstrated in FIG. 6A, exposure of Hep3B cells to conditioned medium from cultured *Spalax* fibroblasts decreased cancer cell growth, while mouse fibroblast conditioned medium had no effect. Importantly, conditioned medium generated by *Spalax* normal fibroblasts gradually suppressed growth of the homologous tumor, *Spalax*-derived fibrosarcoma (FIG. 6B). Further, we evaluated the ability of fibroblasts isolated from *Spalax* or mouse to promote or inhibit cancer cell colony formation in soft agar. Remarkably more colonies were formed when human MCF7 cells were co-cultured with mouse fibroblasts compared to *Spalax* (FIG. 6C). In contrast, a monolayer of *Spalax* fibroblasts reduced MCF7 colony-formation (compared to control).

Figure 6E:
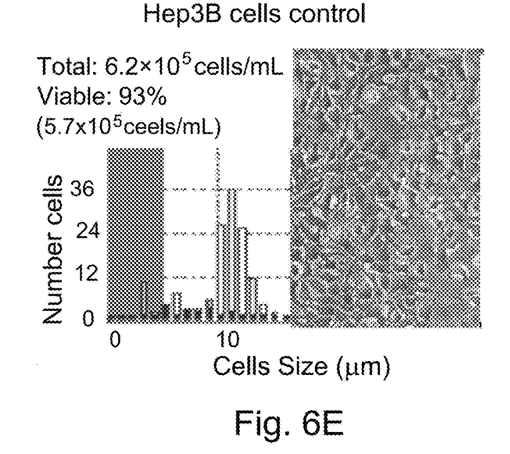

To validate that the cancer-inhibiting effect is not limited to fibroblasts from newborn individuals, we isolated skin fibroblasts from adult *Spalax* (>5.5 years old). The ability of conditioned medium generated by adult *Spalax* fibroblasts to kill Hep3B cells is presented in FIG. 6D. Following 9 days of exposure, both floating and attached cells were collected and their survival rates were determined by a trypan blue extrusion assay. Only 51% of cancer cells incubated under *Spalax* fibroblasts conditioned medium survived while 93% of Hep3B cells incubated in self-conditioned medium (or mice conditioned media) remained adherent and viable (FIG. 6E).

Figure 6F:
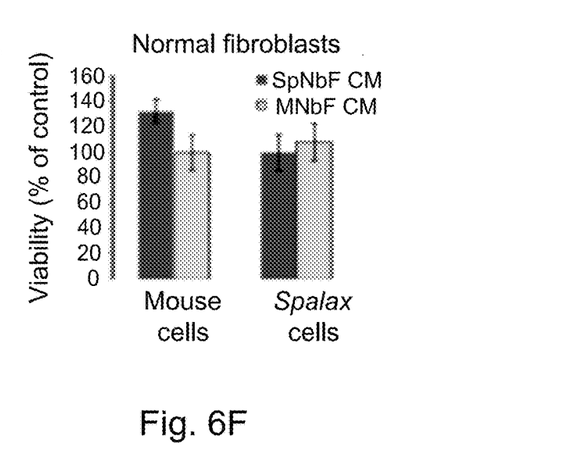
(FIG. 6F) Effects of conditioned media generated by *Spalax* normal fibroblasts on growth of normal fibroblasts. The levels of viability were estimated after 4 days by PRESTO BLUE® reagent, mean±S.D. All results were obtained from three independent experiments performed in 3-6 technical repeats.

We further examined whether *Spalax* fibroblast conditioned medium affects the growth of non-cancerous cells. No inhibitory effect was found when mouse and *Spalax* normal fibroblasts were exposed to conditioned medium generated by *Spalax* fibroblasts (FIG. 6F).

Figure 7:
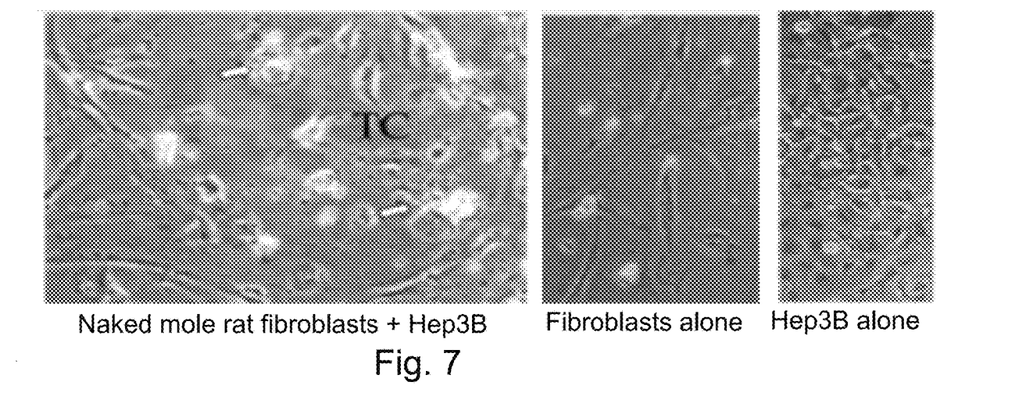
FIG. 7 shows that naked mole rat (*Heterocephalus*) fibroblasts restrict the growth and kill cancer cells in co-culture experiments. Hep3B tumor cells were cultured either alone or in presence of (*Heterocephalus*) fibroblasts in the ratio of 1:10 ($5×10^4$ fibroblasts and $5×10^3$ cancer cells in six-well plates) in RPMI/DMEM-F12 media (1:1) containing 10% FBS. After seven days incubation cells were photographed. Microphotographic images are shown (×200). White arrows point to the foci of damaged cancer cells colonies TC, tumor cells.

Like *Spalax*, naked mole rat fibroblasts also demonstrate anticancer activity presented as destroyed cancer cells when co-cultured together with the naked mole rat's fibroblasts (FIG. 7).

Figure 8:
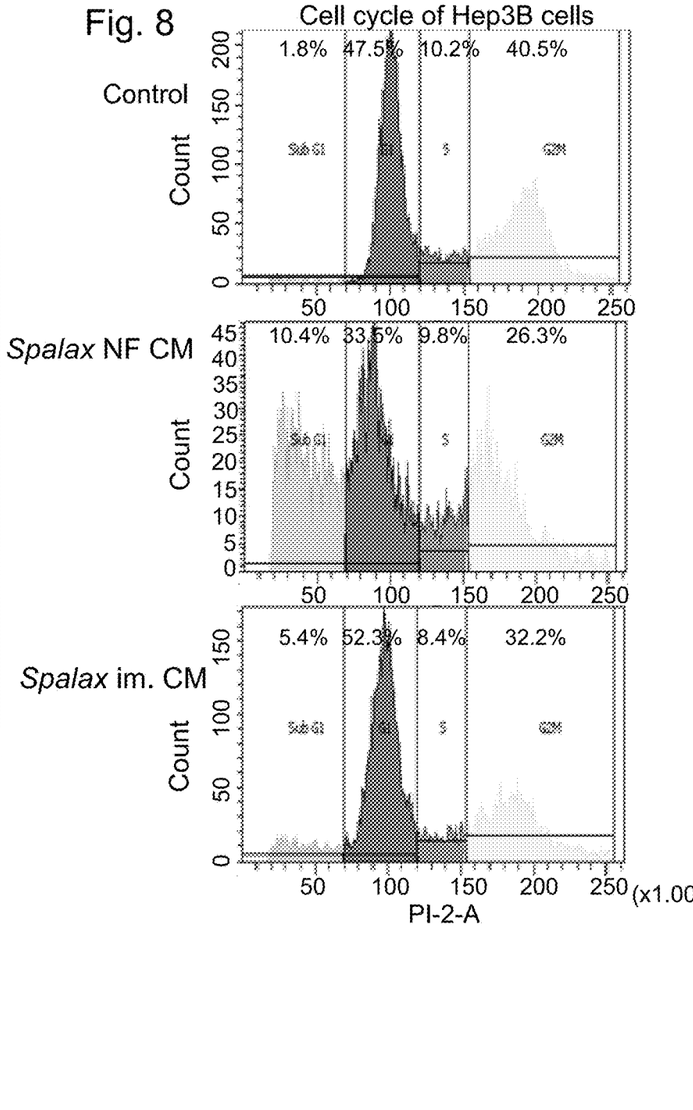
FIG. 8 shows the *Spalax* normal fibroblast-conditioned medium; but not immortalized cells CM, compromises cell cycle, of Hep3B cells. Hep3B cells were grown on cover slips under medium conditioned by *Spalax* normal fibroblast (middle chart) or *Spalax* immortalized fibroblasts (right chart) for seven days. Cells were harvested and stained with propidium iodide, and cells cycles were analyzed by flow cytometry. *Spalax* immortalized (by serial passages) cells lost their ability to inhibit cancer cells.

To investigate the mechanisms by which *Spalax* fibroblasts induce cancer cell death, we examined the cell cycle distributions in Hep3B. No changes in the cell cycle distribution were found when Hep3B cells were incubated with CM generated by immortalized cell line generated from the same fibroblast cancer-affecting primary cells, or when compared to Hep3B grown with their own medium. (FIG. 8). In contrast, following exposure to *Spalax* CM, Hep3B cell cycle analysis revealed a noticeable accumulation of dead cells in sub-G1 (approx. 30%).

Figure 9:
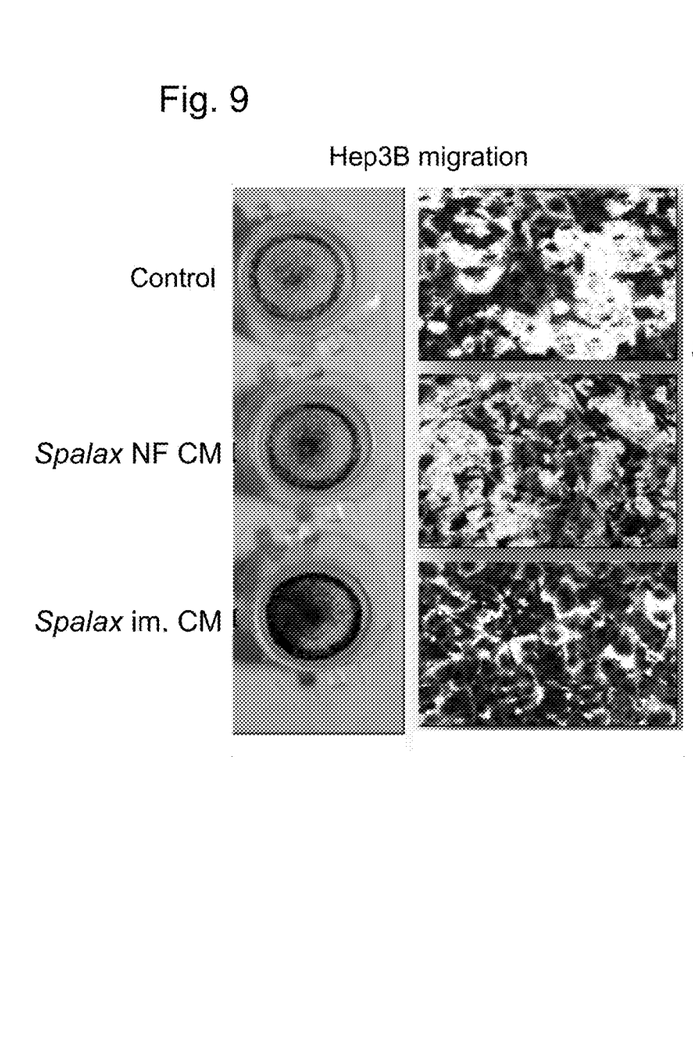
FIG. 9 depicts the effects of *Spalax* normal and immortal fibroblasts on the migration of breast cancer cells MDA-MB-231. Fibroblasts were seeded into 24-well plates (TRANSWELL®, Corning Inc.) at the density of $10^5$ cell/well, incubated 48 h, thereafter the inserts containing $25×10^4$ MDA-MB-231 were immersed in lower chambers without changing medium. 24 hours after the incubated membranes were fixed with 2.5% glutaraldehyde (GA) for 10 min, washed in double-distilled water (DDW), and stained with 0.5% toluidine blue for 5 mm and photographed. Color intensity reflects the cells that crossed to the lower of insert (migrating cells).

Migration assay revealed that *Spalax* normal fibroblasts did not promote the migration of breast cancer cells MDA-MB-231 through a porous membrane (TRANSWELL®, Corning Inc.). In contrast, immortalized cells promoted the invasion of cancer cells towards fibroblasts (FIG. 9).

It will be understood that particular embodiments described herein are shown by way of illustration and not as limitations of the disclosure. The principal features of this disclosure can be employed in various embodiments without departing from the scope of the disclosure.

All publications are herein incorporated by reference to the same extent as if each individual publication was specifically and individually indicated to be incorporated by reference.

REFERENCES

Antonescu, C R, Baren A (2004). Spectrum of low-grade fibrosarcomas: a comparative ultrastructural analysis of low-grade myxofibrosarcoma and fibromyxoid sarcoma. *Ultrastructural pathology.* 28, 321-332.

Avivi A, Ashur-Fabian O, Joel A, Trakhtenbrot L, Adamsky K, Goldstein I, Amariglio N, Rechavi G, Nevo E (2007). P53 in blind subterranean mole rats—loss-of-function versus gain-of-function activities on newly cloned *Spalax* target genes. *Oncogene.* 26, 2507-2512.

Avivi A, Gerlach F, Joel A, Reuss S, Burmester T, Nevo E, Hankeln T (2010). Neuroglobin, cytoglobin, and myoglobin contribute to hypoxia adaptation of the subterranean mole rat *Spalax. Proceedings of the National Academy of Sciences of the United States of America.* 197, 21570-21575.

Avivi A, Shams I, Joel A, Lache O, Levy A P, Nevo E (2005). Increased blood vessel density provides the mole rat physiological tolerance to its hypoxic subterranean habitat. *Faseb J.* 19, 1314-1316.

Flesher J W, Horn J, Lehner A F (1998). Carcinogenicity of 1-hydroxy-3-methylcholanthrene and its electrophilic sulfate ester 1-sulfooxy-3-methylcholanthrene in Sprague-Dawley rats. *Biochem Biophys Res Commun.* 243, 30-35.

Glaysher S, Cree I A (2011). Isolation and culture of colon cancer cells and cell lines. In *Cancer Cell Culture.* (I A Cree, ed). Portsmouth, UK: Humana Press, pp. 135-140.

Goerttler K, Loehrke H, Hesse B, Schweizer J (1984). Skin tumor formation in the European hamster (*Cricetus cricetus* L.) after topical initiation with 7,12-dimethylbenz[a]anthracene (DMBA) and promotion with 12-O-tetradecanoylphorbol-13-acetate (TPA). *Carcinogenesis.* 5, 521-524.

Goerttler K, Loehrke H, Schweizer J, Hesse B (1982). Diterpene ester-mediated two-stage carcinogenesis. *Carcinogenesis; a comprehensive survey,* 7, 75-83.

Izzotti A, Camoirano A, Cartiglia C, Grubbs C J, Lubet R A, Kelloff G J, De Flora S (1999). Patterns of DNA adduct formation in liver and mammary epithelial cells of rats treated with 7,12-dimethylbenz(a)anthracene, and selective effects of chemopreventive agents. *Cancer research.* 59, 4285-4290.

Krelin Y, Voronov E, Dotan S, Elkabets M, Reich E, Fogel M, Huszar M, Iwakura Y, Segal S, Dinarello C A, Apte R N (2007). Interleukin-1beta-driven inflammation promotes the development and invasiveness of chemical carcinogen-induced tumors. *Cancer research.* 67, 1062-1071.

Malik A, Korol A, Hubner S, Hernandez A G, Thimmapuram J, Ali S, Glaser F, Paz A, Avivi A, Band M (2011). Transcriptome sequencing of the blind subterranean mole rat, *Spalax* galili: utility and potential for the discovery of novel evolutionary patterns. *PloS one,* 6, e21227.

Malik A, Korol A, Weber M, Hankeln T, Avivi A, Band M (2012). Transcriptome analysis of the *spalax* hypoxia survival response includes suppression of apoptosis and tight control of angiogenesis. *BMC genomics,* 13, 615.

Malins D C, Anderson K M, Gilman N K, Green V M, Barker E A, Hellstrom K E (2004). Development of a cancer DNA phenotype prior to tumor formation. *Proceedings of the National Academy of Sciences of the Untied States of America.* 101, 10721-10725.

Manov I, Hirsh M, Iancu T C (2004). N-acetylcysteine does not protect HepG2 cells against acetaminophen-induced apoptosis. *Basic Clin Pharmacol Toxicol.* 94, 213-225.

Manov I, Hirsh M, Iancu T C, Malik A, Sotnichenko N, Band M, Avivi A, Shams I (2013). Pronounced cancer resistance in a subterranean rodent, the blind mole-rat, *Spalax*: in vivo and in vitro evidence. *BMC biology.* 11, 91.

Manov I, Pollak Y, Broneshter R, Iancu T C (2011). Inhibition of doxorubicin-induced autophagy in hepatocellular carcinoma Hep3B cells by sorafenib—the role of extracellular signal-regulated kinase counteraction. *FEBS J.* 278, 3494-3507.

Nasser N J, Avivi A, Shafat I, Edovitsky E, Zcharia E, Ilan N, Vlodavsky I, Nevo E (2009). Alternatively spliced *Spalax* heparanase inhibits extracellular matrix degradation, tumor growth, and metastasis. *Proceedings of the National Academy of Sciences of the Untied States of America.* 106, 2253-2258.

Nevo E (1999). *Mosaic Evolution of Subterranean Mammals: Regression, Progression and Global Convergence.* Oxford: Oxford University Press.

Nevo E, Ivanitskaya E, Beiles A (2001). *Adaptive Radiation of Blind Subterranean Mole Rats.* Leiden: Backhuys.

Ravid O, Shams I, Ben Califa N, Nevo E, Avivi A, Neumann D (2007). An extracellular region of the erythropoietin receptor of the subterranean blind mole rat *Spalax* enhances receptor maturation. *Proceedings of the National Academy of Sciences of the United States of America.* 104, 14360-14365.

Schulke S, Dreidax D, Malik A, Burmester T, Nevo E, Band M, Avivi A, Hankeln T (2012). Living with stress: Regulation of antioxidant defense genes in the subterranean, hypoxia-tolerant mole rat, *Spalax, Gene.*

Shams I, Avivi A, Nevo E (2005a). Oxygen and carbon dioxide fluctuations in burrows of subterranean blind mole rats indicate tolerance to hypoxic-hypercapnic stresses. *Comp Biochem Physiol A Mol Integr Physiol.* 142, 376-382.

Shams I, Nevo E, Avivi A (2005b). Ontogenetic expression of erythropoietin and hypoxia-inducible factor-1 alpha genes in subterranean blind mole rats. *Faseb J.* 19, 307-309.

Tyan S W, Kuo W H, Huang C K, Pan C C, Shew J Y, Chang K J, Lee E Y, Lee W H (2011). Breast cancer cells induce cancer-associated fibroblasts to secrete hepatocyte growth factor to enhance breast tumorigenesis. *PloS one.* 6, e15313.

Yuspa S H (1998). The pathogenesis of squamous cell cancer: lessons learned from studies of skin carcinogenesis. *Journal of dermatological science.* 17, 1-7.

The invention claimed is:
1. A pharmaceutical composition comprising:
a conditioned cell culture medium harvested from a culture of primary skin and lung fibroblast cells isolated from *Spalax* or naked mole rat *Heterocephalus*, wherein the culture of fibroblast cells exhibits healthy propagation or absence of fibroblast cell senescence and the conditioned cell culture medium exhibits cancer-suppressing ability,
at least one chemotherapeutic agent, and
a pharmaceutically active carrier, excipient or diluent.

2. The pharmaceutical composition according to claim 1, wherein said fibroblast cells are isolated from *Spalax* ehrenbergi.

3. The pharmaceutical composition according to claim 1, wherein said fibroblast cells are skin or lung fibroblasts.

4. The pharmaceutical composition according to claim 3, wherein said skin or lung fibroblasts are primary cells.

5. A method for treatment of hepatocellular or breast carcinoma in a human subject in need, said method comprising administering to the subject an effective amount of the pharmaceutical composition according to claim 1.

* * * * *